US012805750B2

(12) United States Patent
Smith

(10) Patent No.: US 12,805,750 B2
(45) Date of Patent: Nov. 24, 2026

(54) SMART WEARABLE WITH BLOOD ALCOHOL TESTER

(71) Applicant: Thomas E. Smith, Minneapolis, MN (US)

(72) Inventor: Thomas E. Smith, Minneapolis, MN (US)

( * ) Notice: Subject to any disclaimer, the term of this patent is extended or adjusted under 35 U.S.C. 154(b) by 443 days.

(21) Appl. No.: 18/234,535

(22) Filed: Aug. 16, 2023

(65) Prior Publication Data

US 2024/0315595 A1 Sep. 26, 2024

Related U.S. Application Data

(60) Provisional application No. 63/453,723, filed on Mar. 21, 2023.

(51) Int. Cl.
*A61B 5/097* (2006.01)
*A61B 5/00* (2006.01)

(52) U.S. Cl.
CPC ............ *A61B 5/097* (2013.01); *A61B 5/0022* (2013.01); *A61B 5/4845* (2013.01); *A61B 5/681* (2013.01); *A61B 5/743* (2013.01)

(58) Field of Classification Search
CPC ..... A61B 5/097; A61B 5/0022; A61B 5/4845; A61B 5/681; A61B 5/743
USPC ........................................................ 600/532
See application file for complete search history.

(56) References Cited

U.S. PATENT DOCUMENTS

2010/0063408 A1* 3/2010 Nothacker ......... G01N 33/4972 600/532
2022/0240849 A1* 8/2022 Spector .................. A61B 5/742

* cited by examiner

*Primary Examiner* — Chanel J Yoon
(74) *Attorney, Agent, or Firm* — Westman, Champlin & Koehler, P.A.; Amanda M. Prose

(57) ABSTRACT

A wearable device includes a band, and a smart watch coupled to the band, and having a face and a display. A blood alcohol tester is integrated with the smart watch, the blood alcohol tester coupled to the smart watch to provide blood alcohol reports to the smart watch upon testing for blood alcohol level.

6 Claims, 3 Drawing Sheets

SMART WEARABLE WITH BLOOD ALCOHOL TESTER

CROSS-REFERENCE TO RELATED APPLICATION(S)

This application claims priority to U.S. provisional application No. 63/453,723, filed on Mar. 21, 2023, the content of which is hereby incorporated by reference in its entirety.

SUMMARY

A wearable device includes a band, and a smart watch coupled to the band, and having a face and a display. A blood alcohol tester is integrated with the smart watch, the blood alcohol tester coupled to the smart watch to provide blood alcohol reports to the smart watch upon testing for blood alcohol level.

A method of testing blood alcohol content with a wearable device includes providing the wearable device with a breathalyzer blood alcohol tester integrated with an operating system of the wearable device. A port coupler and attached tube are rotated from a stowed position to an active position. The port is opened by a predetermined motion of the port coupler and attached tube. The blood alcohol is tested by blowing into the breath tube.

This summary is not intended to describe each disclosed embodiment or every implementation of wearable blood alcohol testers as described herein. Many other novel advantages, features, and relationships will become apparent as this description proceeds. The figures and the description that follow more particularly exemplify illustrative embodiments.

DETAILED DESCRIPTION OF ILLUSTRATIVE EMBODIMENTS

Figure 1:
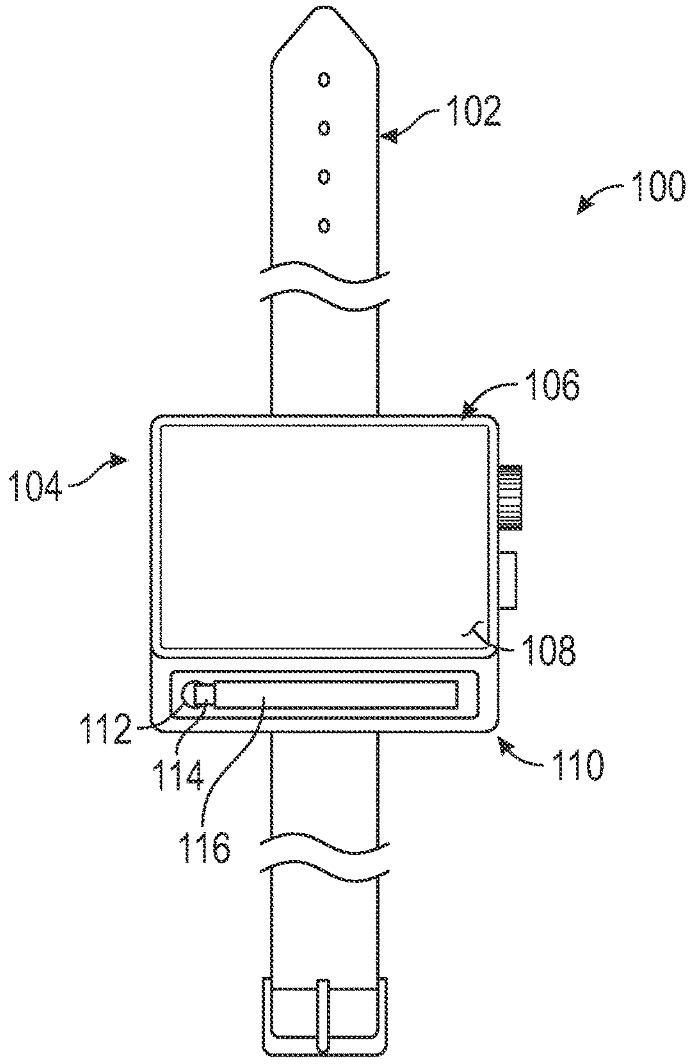
FIG. 1 is a top elevation view of a wearable device with blood alcohol tester according to an embodiment of the present disclosure.

In general, embodiments of the present disclosure provide a blood alcohol breathalyzer type blood alcohol tester in a wearable smart watch. The watch itself may be any type of wearable smart watch, such as but not limited to FitBit, AppleWatch, or the like. In addition to its typical smart watch capabilities, embodiments of the present disclosure provide a portion of the watch face with a visible blood alcohol breathalyzer type tester.

Alcoholic drinks are a favorite beverage of many people. Unfortunately, when alcohol is consumed to excess, bad decisions often result. The drinker may decide to drive, call someone and say things that should not be sad, or buy things on impulse that can cause additional financial, physical, or emotional hardship. Most people do not start out wanting to end up in an inebriated state, but parameters such as time, consumption of food, unknown alcohol levels in drinks and the lake can all affect a person in different ways. The only sure way of determining blood alcohol level is via a breathalyzer or blood test. Unfortunately, such testing means are not always available, and even if they are, they are not discreet to use. Accordingly, there exists a need for a blood alcohol tester that may be used at any time in a discreet manner.

When a person is in a position where they have been consuming alcohol, there are some portable options for making a quick test of blood alcohol content. However, many such devices are not immediately accessible, and may not be remembered when the time comes to operate a vehicle. Such options include pocket sized breathalyzers, such as may be carried in a pocket, purse, or the like, or stowed in a glove box or center console of a vehicle. When such items are not in plain sight, they may be much more likely not to be used, as the potential user may momentarily forget to use them, or forget they are even available.

In contrast, most watch users refer to their watches multiple time an hour, or even more, such as to check the time, to review text message that has been received, taking a phone call, when a reminder or the like is provided, when a fitness app on the watch indicates it is time for some movement, and the like. Accordingly, most smart watch users are much more likely to look at their smart watches routinely, and often many times during the course of an hour or a night out. As such, a smart watch that has a breathalyzer type blood alcohol tester on the actual face of the watch is much more likely to be used, as it will be in the mid of a potential user many times over the course of multiple checks of the smart watch.

In one embodiment, the watch includes a breathalyzer with requisite components for analysis and connections to the smart watch to display readings of blood alcohol content. In one embodiment, a port is provided in a watch face with a replaceable tube that connects to the port and folds down to be stored when not in use. The port is coupled to received breath blown through the tube to the breathalyzer for analysis. When not in use, the tube connected to the port is stowed in a cavity or other opening so as to render the watch flat or nearly flat for regular use. When it is desired to use the breathalyzer to It should be noted that the same reference numerals are used in different figures for same or similar elements. It should also be understood that the terminology used herein is for the purpose of describing embodiments, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the embodiments thereof. For example, "first." "second," and "third" elements or steps need not necessarily appear in that order, and the embodiments thereof need not necessarily be limited to three elements or steps. It should also be understood that, unless indicated otherwise, any labels such as "left." "right," "front," "back," "top." "bottom," "forward," "reverse," "clockwise," "counter clockwise," "up," "down," or other similar terms such as "upper," "lower," "aft." "fore," "vertical," "horizontal," "proximal," "distal," "intermediate" and the like are used for convenience and are not intended to imply, for example, any particular fixed location, orientation, or direction. Instead, such labels are used to reflect, for example, relative location, orientation, or directions. It should also be understood that the singular forms of "a." "an," and "the" include plural references unless the context clearly dictates otherwise.

FIG. 1 is a perspective view of smart wearable device 100 with breathalyzer. The device 100 comprises in one embodiment a band 102 and a smart watch 104, the smart watch 104 coupled to the band 102, and having a face 106 with a display 108. A blood alcohol tester 110 is integrated with the smart watch, in one embodiment on the face 106. The blood alcohol tester 110 is coupled to the smart watch 104 to provide blood alcohol reports to the smart watch 104 upon testing for blood alcohol level with the blood alcohol tester 110. In one embodiment, the blood alcohol tester 110 is a breathalyzer.

Figure 2:
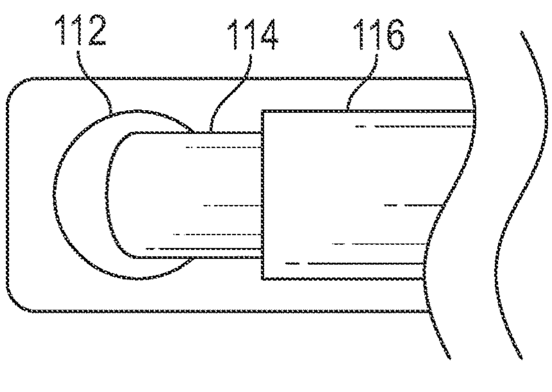
FIG. 2 is an expanded view of a port, port coupler, and tube of the blood alcohol tester of FIG. 1 according to an embodiment of the present disclosure.
Figure 3:
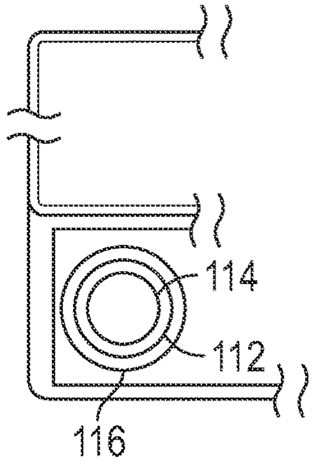
FIG. 3 is a top view of a portion of the wearable device with the port coupler and tube in an active position.
Figure 4:
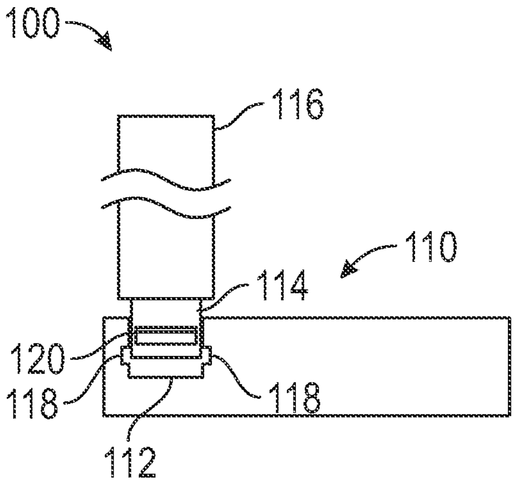
FIG. 4 is a side view of FIG. 3.
Figure 5:
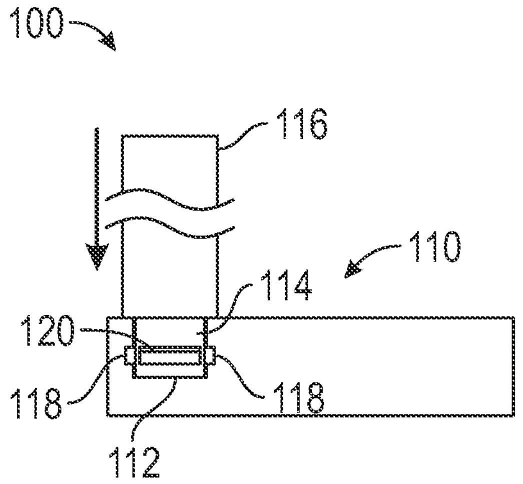
FIG. 5 is a side view of the port coupler and tube once pressed into the port.
Figure 6:
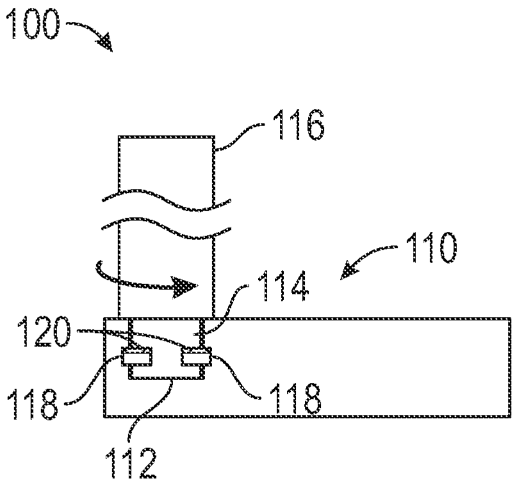
FIG. 6 is a side view of the port coupler and tube twisted in the port to open the blood alcohol tester.
Figure 7:
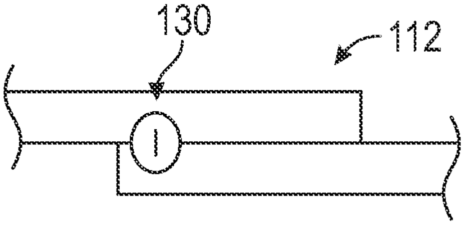
FIG. 7 is a side view of a locking clasp according to an embodiment of the present disclosure.

The breathalyzer contains circuitry and systems common to breathalyzers to allow it to accurately read a user's blood alcohol level. In one embodiment, the breathalyzer 110 is actuated and accessed through a port 112 that is normally closed, a port coupler 114 rotatable from a first stowed position (FIGS. 1-2) to a second active position (FIGS. 3-5), and a tube 116 coupleable to the port coupler 114. In one embodiment, the port 112 is openable via rotating the port coupler 114 and tube 116 from the first stowed position to the second active position, pressing the tube and coupler down, and twisting the tube and port coupler to "snap in" to the port 112. In one embodiment the port 112 has detents 118 into which projections 120 on the port coupler 114 snap to allow for twisting of the coupler 114 and tube 116 to open a passage 122 for air breathed into the tube 116 to pass into the breathalyzer 110 via tube 116, port coupler 114, and opening 122 in port 112 effected by the opening motion described above. It should be understood that different opening mechanisms may be employed without departing from the scope of the disclosure, and that such opening mechanisms would be evident to one of skill in the art, and as such, are not described further herein. When the test is complete, the tube 116 may be replaced, or not, and the tube 116 and port coupler 114 rotated to release from the port 112. Then, the tube 116 and port coupler 114 may be rotated from the active position to the stowed position for later use. When the port coupler and tube are rotated to the stowed position, the blood alcohol tester is turned off or to an inactive/standby mode. This may be accomplished through sensing, through a period of inactivity, through the app, or the like, without departing from the scope of the disclosure.

In one embodiment, the smart watch 104 is coupled to display output from the blood alcohol tester 110 on the display 108 when the blood alcohol tester is used. In this embodiment, the smart watch 104 and the blood alcohol tester 110 operate and/or interact with an app on the smart watch 104 that is configured to communicate with and store and monitor readings from the blood alcohol tester. In another embodiment, the wearable device 100 is configured to pair to an external cellular telephone for maintaining records related to the blood alcohol tester 110.

In another embodiment, the blood alcohol tester 110 and/or the app operable on the smart watch 104 is configured to use Bluetooth, WIFI, cellular, or other wireless communication to make at least one notification of a determined blood alcohol content not only to the display 108 of the smart watch 104, but also to a third party, upon use of the blood alcohol tester.

In another embodiment, a clasp lock 130 may be used on the band 102 to releasably lock the band 102 and therefore the wearable device 100 to a wrist of a user. While a clasp lock is shown, it should be understood that different locking mechanisms may be used without departing from the scope of the disclosure, and that such locking mechanisms would be evident to one of skill in the art, and as such, are not described further herein. The locking on of the wearable device to the wrist of the user facilitates any required type of testing by not allowing the user to remove the device.

For example, a person under guardianship, underage, or the like, may be required to have the wearable device on their wrist, and to test at a certain time. Should the test not occur, the wearable device may in one embodiment notify a third party that the test did not occur. Alternatively, the wearable device can communicate to the third party results of such a test.

Figure 8:
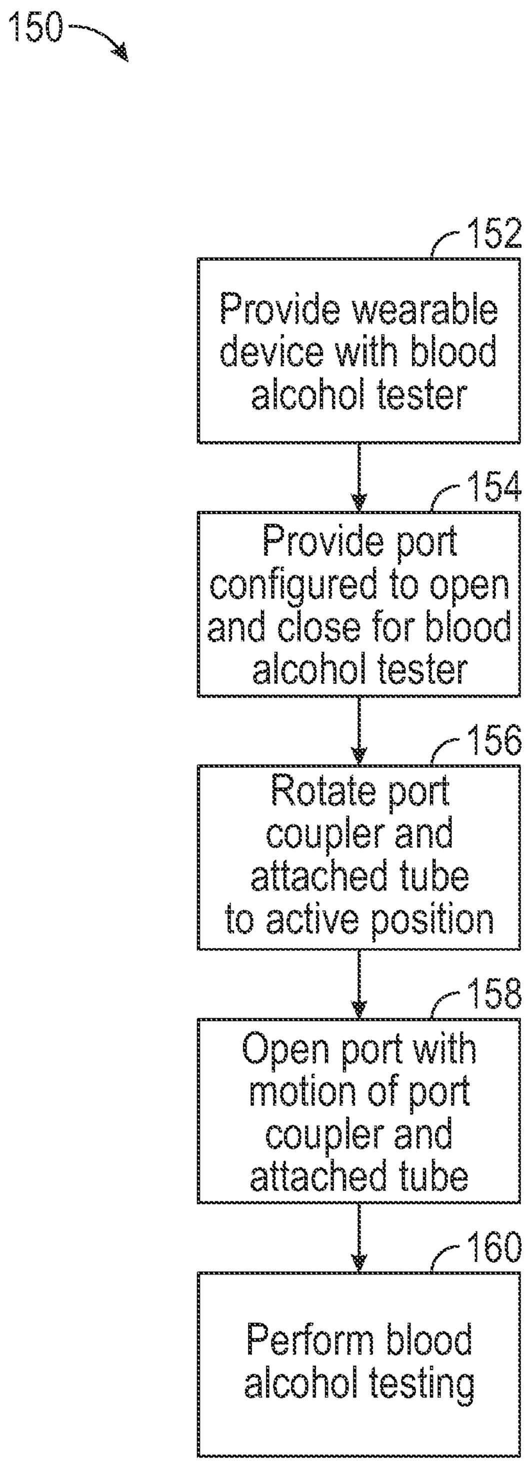
FIG. 8 is a flow chart diagram of a method according to an embodiment of the present disclosure.

A method 150 of testing blood alcohol content with a wearable device blood alcohol tester is shown in flowchart form in FIG. 8. Method 150 comprises, in one embodiment, providing the wearable device with a breathalyzer blood alcohol tester integrated with an operating system of the wearable device in block 152, and providing a port configurable to open and close for access to the breathalyzer in block 154. A port coupler and attached tube are rotated to an active position from a stowed position in block 156, the port is opened with a predetermined motion of the port coupler and attached tube to activate the breathalyzer in block 158, and blood alcohol testing is performed by blowing into the breath tube to test blood alcohol level in block 160. In one embodiment the predetermined motion of the port coupler and attached tube is pressing and twisting the port coupler and breath tube to open the port as described above.

The method further comprises in one embodiment the wearable device displaying output from the blood alcohol tester upon use thereof. The method further comprises in one embodiment the wearable device pairing to a cellular telephone for maintaining records related to the blood alcohol tester. The method further comprises in one embodiment the wearable device operating an application configured to store and monitor readings from the blood alcohol tester. The method further comprises in one embodiment the blood alcohol tester using the wearable device to make at least one notification of a determined blood alcohol content to a third party upon use of the blood alcohol tester.

Other features of wearable devices such as smart watches, such as but not limited to taking blood pressure, pulse, providing access to the Internet, telephone, messaging, and the like are available in embodiments of the present disclosure. The embodiments are capable of being wirelessly coupled to a smart phone, or operated directly from the smart watch. The wearable device with breathalyzer according to embodiment of the present disclosure appears as a conventional smart watch with a band, display, control switches, rechargeable battery, and the like. The embodiments can report date, time, and other parameters to any paired smart phone. In addition to all functions of a traditional smart watch, embodiment of the present disclosure are equipped with a breathalyzer accessible via a port in the face of the watch, the breathalyzer function is accessed via connection of a tube to the port, rotation of the tube to make it accessible, and a correction and opening of the port via some mechanism, such as pressing the tube and twisting it to open the port. Once the port is open, the breathalyzer function of the watch is activated, and a breath test may be effected by blowing into the tube for a specified period of time. Once activated, the watch display, or a separate display for the breathalyzer, may be used to provide instructions on its operation. Once the test is complete, the tube and port may be deactivated, and the tube folded back to a stored position. Replacement tubes for use with additional tests may also be provided.

The above-disclosed subject matter is to be considered illustrative, and not restrictive, and the appended claims are intended to cover all such modifications, enhancements, and other embodiments, which fall within the true scope of the present disclosure. Thus, to the maximum extent allowed by law. the scope of the present disclosure is to be determined by the broadest permissible interpretation of the following claims and their equivalents, and shall not be restricted or limited by the foregoing detailed description.

What is claimed is:

1. A wearable device, comprising:

a band; and a smart watch coupled to the band, and having a face and a display; and a blood alcohol tester integrated with the smart watch, the blood alcohol tester coupled to the smart watch to provide blood alcohol reports to the smart watch upon testing for blood alcohol level, wherein the blood alcohol tester is a breathalyzer comprising:

a port that is normally closed;

a port coupler rotatable from a first stowed position to a second active position;

a replaceable tube coupleable to the port coupler; and a port opening mechanism that is actuated by moving the port coupler from the first stowed position to the second active position, coupling the replaceable tube to the port coupler, whereby pressing the replaceable tube and port coupler opens the port, and twisting the replaceable tube and port coupler then activates the breathalyzer.

2. The wearable device of claim 1, wherein the smart watch is configured to display an output from the blood alcohol tester upon use thereof.

3. The wearable device of claim 1, and further comprising a lock for the band, the lock configured to retain the wearable device on a wrist of a user.

4. The wearable device of claim 1, wherein the wearable device is configured to pair to a cellular telephone for maintaining records related to the blood alcohol tester.

5. The wearable device of claim 1, wherein the wearable device includes an application to store and monitor readings from the blood alcohol tester.

6. The wearable device of claim 5, wherein the blood alcohol tester is configured to use the smart watch to make at least one notification of a determined blood alcohol content to a third party upon use of the blood alcohol tester.

* * * * *